United States Patent [19]
Burkoth et al.

[11] Patent Number: 5,785,991
[45] Date of Patent: Jul. 28, 1998

[54] SKIN PERMEATION ENHANCER COMPOSITIONS COMPRISING GLYCEROL MONOLAURATE AND LAURYL ACETATE

[75] Inventors: Terry L. Burkoth; Lina T. Taskovich, both of Palo Alto; Nieves Crisologo, Sunnyvale, all of Calif.

[73] Assignee: Alza Corporation, Palo Alto, Calif.

[21] Appl. No.: 481,549

[22] Filed: Jun. 7, 1995

[51] Int. Cl.$^6$ .................................. A61F 13/02
[52] U.S. Cl. ................. 424/448; 424/449; 514/946; 514/947
[58] Field of Search ........................ 424/448, 449; 514/946, 947

[56] References Cited

U.S. PATENT DOCUMENTS

| | | | |
|---|---|---|---|
| 3,472,931 | 10/1969 | Stoughton et al. | 424/180 |
| 3,527,864 | 9/1970 | MacMillan et al. | 424/177 |
| 3,598,122 | 11/1982 | Zaffaroni | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/361 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/895 |
| 4,559,222 | 12/1985 | Enscore et al. | 424/28 |
| 4,568,343 | 2/1986 | Leeper et al. | 604/896 |
| 4,573,995 | 3/1986 | Chen et al. | 604/896 |
| 4,588,580 | 5/1986 | Gale et al. | 424/21 |
| 4,645,502 | 2/1987 | Gale et al. | 604/896 |
| 4,704,282 | 11/1987 | Campbell et al. | 424/449 |
| 4,746,515 | 5/1988 | Cheng et al. | 424/449 |
| 4,788,052 | 11/1988 | Gale et al. | 424/449 |
| 4,816,258 | 3/1989 | Nedberge et al. | 424/448 |
| 4,820,720 | 4/1989 | Sanders et al. | 514/356 |
| 4,849,226 | 7/1989 | Gale | 424/448 |
| 4,863,738 | 9/1989 | Taskovich | 424/449 |
| 4,863,970 | 9/1989 | Patel | 514/784 |
| 4,908,027 | 3/1990 | Enscore et al. | 604/890.1 |
| 4,943,435 | 7/1990 | Baker et al. | 424/448 |
| 4,954,487 | 9/1990 | Cooper et al. | 514/159 |
| 5,004,610 | 4/1991 | Osborne et al. | 424/448 |
| 5,020,556 | 6/1991 | Drust et al. | 424/449 |
| 5,122,382 | 6/1992 | Gale et al. | 424/449 |
| 5,149,538 | 9/1992 | Granoer | 424/449 |
| 5,162,410 | 11/1992 | Sweet | 524/266 |

(List continued on next page.)

FOREIGN PATENT DOCUMENTS

| | | | |
|---|---|---|---|
| 0043738 | 1/1982 | European Pat. Off. | A61K 9/06 |
| 1001949 | 8/1965 | Germany | A61K 3/00 |
| 9509006 | 4/1995 | WIPO | A61K 47/14 |

OTHER PUBLICATIONS

Shah, Hemanshu S., et al., Drug Development and Industrial Pharmacy, vol. 18, No. 12, pp. 1461–1476 (1992), "Enhancement of In Vitro Skin Permeation of Verapamil".

Idson, Bernard, Journal of Pharmaceutical Sciences, Jun. 1975, vol. 64, No. 6, pp. 901–924, "Percutaneous Absorption".

*Primary Examiner*—D. Gabrielle Phelan
*Attorney, Agent, or Firm*—Michael J. Rafa; Paul L. Sabatine; Steven F. Stone

[57] ABSTRACT

Compositions, devices, and methods for transdermal administration of an active agent are disclosed using a novel dual permeation enhancer mixture comprising lauryl acetate and a monoglyceride, preferably glycerol monolaurate. The dual permeation enhancer mixture comprising lauryl acetate is a potent permeation enhancer and provides stable systems which are more readily characterized.

34 Claims, 5 Drawing Sheets

U.S. PATENT DOCUMENTS

| | | | |
|---|---|---|---|
| 5,198,223 | 3/1993 | Gale et al. | 424/449 |
| 5,314,694 | 5/1994 | Gale | 424/448 |
| 5,320,850 | 6/1994 | Gale et al. | 424/449 |
| 5,352,456 | 10/1994 | Fallon et al. | 424/448 |
| 5,376,377 | 12/1994 | Gale et al. | 424/448 |
| 5,378,730 | 1/1995 | Lee et al. | 514/535 |

SKIN PERMEATION ENHANCER COMPOSITIONS COMPRISING GLYCEROL MONOLAURATE AND LAURYL ACETATE

TECHNICAL FIELD

This invention relates to the transdermal delivery of drugs or other biologically active agents and more particularly to methods and compositions for enhancing the percutaneous absorption of drugs or other agents when incorporated in transdermal drug delivery systems or devices. More particularly, this invention relates to the transdermal delivery of drugs utilizing a novel dual permeation enhancer comprising glycerol monolaurate and lauryl acetate.

DESCRIPTION OF TERMS

As used herein, the term "transdermal" means both percutaneous delivery of drug or active agent through skin or mucosal tissue into the circulation by topical application.

As used herein, the term "therapeutically effective" amount or rate refers to the amount or rate of drug or active agent needed to achieve a desired therapeutic result.

As used herein, the phrase "sustained time period" refers to at least about 12 hours and more typically a period in the range of about one to about seven days.

As used herein, the phrase "predetermined area of skin" refers to a defined area of intact unbroken skin or mucosal tissue. That area is usually be in the range of about 5 cm$^2$ to about 100 cm$^2$.

BACKGROUND ART

The transdermal route of parenteral delivery of drugs provides many advantages, and transdermal systems for delivering a wide variety of drugs or other beneficial agents are described in U.S. Pat. Nos. 3,598,122; 3,598,123; 3,731,683; 3,797,494; 4,286,592; 4,314,557; 4,379,454; 4,435,180; 4,559,222; 4,568,343; 4,573,999; 4,588,580; 4,645,502; 4,704,282; 4,816,258; 4,849,226; 4,908,027; 4,943,435; and 5,004,610, for example, all of which are incorporated herein by reference. In many cases, drugs which would appear to be ideal candidates for transdermal delivery are found to have such low permeability through intact skin that they cannot be delivered in therapeutically effective amounts from reasonably sized devices.

In an effort to increase skin permeability so that drugs can be delivered in therapeutically effective amounts at therapeutically effective rates, it has been proposed to pretreat the skin with various chemicals or to concurrently deliver the drug in the presence of a permeation enhancer. Various materials have been suggested for this, as described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, "Percutaneous Absorption," J. *Pharm. Sci.* (1975) 64:901–924.

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5–50 cm$^2$) is at therapeutic levels. Additionally, the enhancer when applied to the skin surface, should be non-toxic, non-irritating on prolonged exposure and under occlusion, and non-sensitizing on repeated exposure. Preferably, it should be odorless and capable of delivering drugs without producing burning or tingling sensations.

It is often difficult to predict which compounds will work as permeation enhancers and which permeation enhancers will work for particular drugs. In systemic drug delivery applications, a compound that enhances the permeability of one drug or a family of drugs may not necessarily enhance the permeability of another drug or family of drugs. Therefore, the usefulness of a particular compound as a permeation enhancer must be analyzed carefully.

U.S. Pat. No. 4,954,487 and European Patent Application 0 043 738 disclose pharmaceutical compositions containing a penetrating vehicle consisting essentially of a $C_1$–$C_4$ diol compound and a cell envelope disordering compound. Lauryl acetate is disclosed as a suitable cell envelope disordering compound.

U.S. Pat. No. 5,026,556 discloses a composition for the transdermal delivery of buprenorphine comprising an amount of buprenorphine in a carrier comprising a polar solvent material selected from the group consisting of $C_3$–$C_4$ diols, $C_3$–$C_6$ triols, and mixtures thereof; and a polar lipid material selected from the group consisting of fatty alcohol esters, fatty acid esters, and mixtures thereof. Lauryl acetate is disclosed as a suitable polar lipid material.

U.S. Pat. No. 5,149,538 discloses the transdermal delivery of an opioid. Preferred permeation enhancers are saturated and unsaturated fatty alcohols, fatty alcohol esters, or fatty acids having 8–18 carbon atoms. All of the aforementioned patents are incorporated herein in their entirety by reference.

While it is known in the art to combine permeation enhancers, this invention utilizes a novel combination of dodecyl acetate (lauryl acetate) and glycerol monolaurate (GML), and the combined effect is a significant and surprising improvement over use of GML or lauryl acetate alone.

DISCLOSURE OF THE INVENTION

It has been found that GML, known to enhance drug permeation in vitro, has been erratic and not as effective in vivo. Results derived from in vivo testing using GML as a permeation enhancer have not been found to be as consistent as the results from in vitro tests. Cosolvents such as lauryl lactate, ethyl lactate, myristyl lactate, and ethyl laurate all effectively enhance drug permeation when combined with GML. However, these combinations of cosolvents and GML give inconsistent data from one lot of formulations to another.

One hypothesis for this inconsistency of data may be attributed to the fact that these cosolvents are not obtainable at a high degree of purity. The lauryl lactate used in the Examples that follow, for example, was obtained as two different mixtures: Ceraphyl 31 or a purer lauryl lactate (both from ISP Van Dyk, Bellevue, N.J.). Ceraphyl 31 is a mixture of 50.6% lauryl lactate, 19.1% myristyl lactate, 8.8% lauryl alcohol, 8.3% palmityl lactate, 3.7% stearyl lactate, and 3.5% myristyl alcohol. The purer lauryl lactate is available as a mixture of 82.8% lauryl lactate, 11% lauryl lactyllactate, and 4% 1-dodecanol.

In addition to the problem of inconsistent results, the failure to obtain a cosolvent at a high degree of purity also makes it difficult to characterize the system in which the mixture is used. For this reason alone it may be desirable to find a substitute for cosolvents such as Ceraphyl 31. A cosolvent obtainable at a high degree of purity may overcome the problems of inconsistency, and at the same time provide a system which is more readily characterized.

Accordingly, the present invention provides a composition of matter for application to a body surface or membrane to deliver at least one drug, at a therapeutically effective rate, by permeation through the body surface or membrane, comprising at least one drug and a permeation-enhancing amount of lauryl acetate and a monoglyceride or mixture of monoglycerides of a fatty acid. The invention further provides a method for the transdermal coadministration of a drug at a therapeutically effective rate together with a skin permeation-enhancing amount of lauryl acetate and a monoglyceride or mixture of monoglycerides of a fatty acid. The monoglyceride is preferably glycerol monolaurate.

It is accordingly an aspect of this invention to provide a permeation enhancer composition for use in transdermal compositions, methods, and devices which provides for the transdermal coadministration of a drug at a therapeutically effective rate with improved in vivo efficacy.

It is another aspect of this invention to provide a permeation enhancer composition for use in transdermal compositions, methods, and devices comprising a monoglyceride or mixture of monoglycerides of a fatty acid and a cosolvent wherein the cosolvent is stable and obtainable at a high degree of purity, thus resulting in systems which are more readily characterized.

It is yet another aspect of this invention to provide a permeation enhancer composition for use in transdermal compositions, methods, and devices which provides consistent results from one lot of formulations to another.

These and other aspects and advantages of this invention will be readily apparent from the following description with reference to the accompanying figures.

MODES FOR CARRYING OUT THE INVENTION

Figure 1:
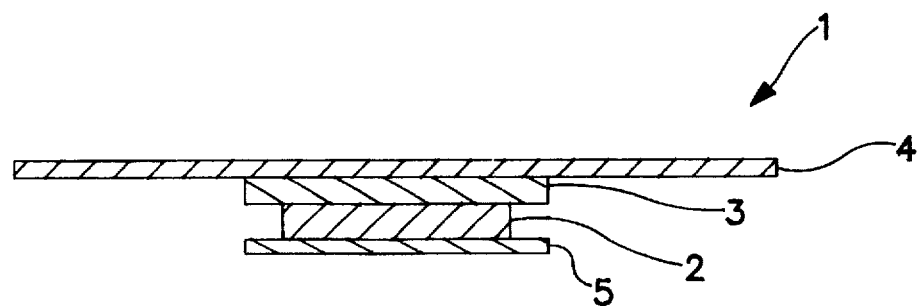
FIG. 1 is a cross-sectional view of one embodiment of a transdermal therapeutic drug delivery device which may be used in accordance with the present invention.

According to the invention, GML is combined with lauryl acetate as a cosolvent to provide an improved permeation enhancer mixture. Lauryl acetate, obtainable at 97–99% purity, is effective as a cosolvent for GML and effectively enhances the permeation of various drugs through the skin. The combination of lauryl acetate and GML is a potent permeation enhancer mixture which is non-irritating to the skin, provides consistent results, and provides a system which is more readily characterized than other GML/cosolvent mixtures using cosolvents of lower purity.

In addition to its higher degree of purity, lauryl acetate also has greater stability than lauryl lactate and can solubilize a larger amount of GML, thus it may allow for a greater amount of GML to reach the skin. A preferred permeation enhancer composition of this invention comprises lauryl acetate of about 97–99% purity together with GML.

It has now been found that a combination of GML and lauryl acetate can be used to effectively enhance the permeability of drugs through body surfaces and particularly through the skin. Specifically, it has been found that GML and lauryl acetate enhance the permeability of the skin such that therapeutically effective amounts of a drug can be delivered from reasonably sized devices at therapeutically effective rates.

The system of the invention is preferably a transdermal drug delivery device comprising a matrix adapted to be placed in drug- and permeation enhancer-transmitting relation with the skin or mucosa. The system must be of a size useful for the application of the drug and the enhancer to a human body.

The utility of a GML/lauryl acetate dual permeation enhancer has been demonstrated for a variety of different drugs as seen in the Examples that follow. It is believed that this invention has utility in connection with the delivery of drugs within the broad class normally delivered through body surfaces and membranes, including skin. In general, this includes therapeutic agents in all of the major areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbituates, benzodiazepines, benzothiadiazides, beta-adrenergic agonists, betaadrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, opiod analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compunds, drugs affecting uterine motility, vasodilators, vitamins and the like.

Representative drugs include, by way of example and not for purposes of limitation, bepridil, diltiazem, felodipine, isradipine, nicardipine, nifedipine, nimodipine, nitredipine, verapamil, dobutamine, isoproterenol, carterolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6α-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, lidocaine, mepivacaine, pramoxine, prilocaine, procaine, proparacaine, tetracaine, alfentanil, choroform, clonidine, cyclopropane, desflurane, diethyl ether, droperidol, enflurane, etomidate, fentanyl, halothane, isoflurane, ketamine hydrochloride, meperidine, methohexital, methoxyflurane, morphine, propofol, sevoflurane, sufentanil, thiamylal, thiopental, acetaminophen, allopurinol, apazone, aspirin, auranofin, aurothioglucose, coichicine, diclofenac, diflunisal, etodolac, fenoprofen, flurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxicam, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, disopyramide, encainide, flecainide, indecainide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinitrate, nitroglycerin, theophylline, phenylephrine, ephidrine, pilocarpine, furosemide, tetracycline, chlorpheniramine, ketorolac, bromocriptine, guanabenz, prazosin, doxazosin, and flufenamic acid.

Other representative drugs include benzodiazepines, such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam, and the like; an antimuscarinic agent such as anisotropine, atropine, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17β-estradiol (or estradiol), semisynthetic estrogen derivatives such as the esters of natural estrogen, such as estradiol-17β-enanthate, estradiol-17β-valerate, estradiol-3-benzoate, estradiol-17β-undecenoate, estradiol 16,17-hemisuccinate or estradiol-17β-cypionate, and the 17-alkylated estrogens, such as ethinyl estradiol, ethinyl estradiol-3-isopropylsulphonate, and the like; an androgen such as danazol, fluoxymesterone, methandrostenolone, methyltestosterone, nandrolone decanoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like.

Lauryl acetate has been demonstrated herein as a suitable cosolvent for GML. Lauryl acetate may also be used as a cosolvent together with other monoglycerides. Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% and a total monoesters content of 58%.

Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. As used herein and in the appended claims, the term "monoglyceride" refers to a monoglyceride or a mixture of monoglycerides of fatty acids.

Transdermal drug delivery systems are typically maintained in contact with the skin using an "in-line" contact adhesive, ie, a layer of adhesive positioned between the drug reservoir of the delivery system and the skin. Glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the second permeation enhancer, the glycerol monooleate must have a total monoesters content of at least 65%.

Administration of the drug according to the invention comprises administering the drug at a therapeutically effective rate to an area of a body surface (eg, skin) or membrane and simultaneously administering GML and lauryl acetate to the area of the body surface or membrane at rates which are sufficient to substantially increase the permeability of the area to the drug formulation.

According to the invention, the GML and lauryl acetate mixture and the drug to be delivered are placed in drug- and permeation enhancer-transmitting relationship to the appropriate body surface, preferably in a carrier therefor, and maintained in place for the desired period of time. The drug and permeation enhancer mixture are typically dispersed within a physiologically compatible matrix or carrier which may be applied directly to the body surface or skin as an ointment, gel, cream, suppository or sublingual or buccal tablet, for example, but are more preferably administered from a transdermal therapeutic delivery device as more fully described below. When used in the form of a liquid, ointment, cream, or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of typical compositions as are known to the art.

The GML/lauryl acetate dual permeation enhancer of this invention has a permeation-enhancing effect on the transport of drugs through body surface tissues generally, in addition to the skin. However, because skin is one of the most effective barriers to the permeation of drugs into the body, the effect of GML and lauryl acetate on skin permeation makes it extremely useful in transdermal delivery. The following description of embodiments of the invention is therefore directed primarily to improving systemic delivery of these drugs by permeation through the skin.

Figure 3:
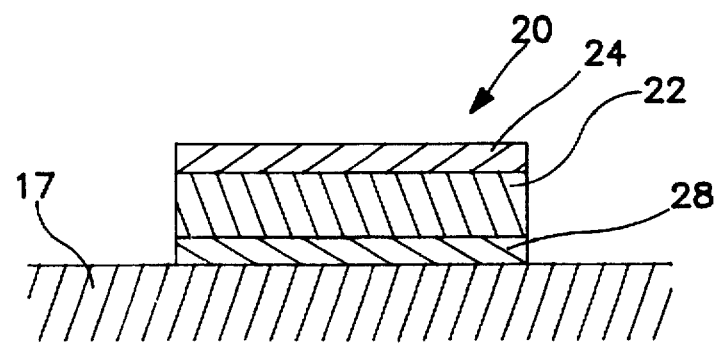
FIG. 3 is a cross-sectional view of yet another embodiment of a transdermal therapeutic drug delivery device which may be used in accordance with this invention.

One embodiment of a transdermal delivery device of the present invention is illustrated in FIG. 1. In FIG. 1, device 1 is comprised of a drug- and permeation enhancer-containing reservoir ("drug reservoir") 2 which is preferably in the form of a matrix containing the drug and the enhancer dispersed therein. An impermeable backing layer 3 is provided adjacent one surface of drug reservoir 2. Adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. Impermeable backing layer 3 is preferably slightly larger than drug reservoir 2, and in this manner prevents the materials in drug reservoir 2 from adversely interacting with the adhesive in overlay 4. A strippable or removable liner 5 is also provided with device 1 and is removed just prior to application of device 1 to the skin.

Figure 2:
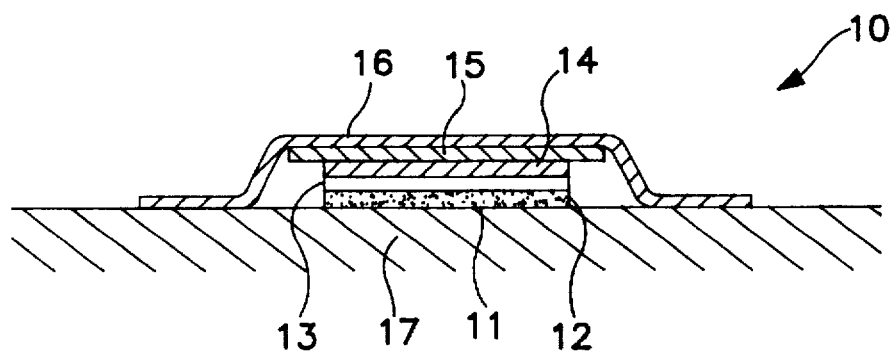
FIG. 2 is a cross-sectional view of another embodiment of a transdermal therapeutic drug delivery device which may be used in accordance with the present invention.

FIG. 2 illustrates another embodiment of the invention, device 10, shown in placement on the skin 17. In this embodiment, the transdermal drug delivery device 10 comprises multi-laminate drug formulation/enhancer reservoir 11 having at least two zones 12 and 14. Zone 12 consists of a drug reservoir substantially as described with respect to FIG. 1. Zone 14 comprises a permeation enhancer reservoir which is preferably made from substantially the same matrix as is used in zone 12. Zone 14 comprises GML and lauryl acetate dispersed throughout and is substantially free of any undissolved drug. A rate-controlling membrane 13 for controlling the release rate of the GML/lauryl acetate mixture from zone 14 to zone 12 is placed between the two zones. A rate-controlling membrane (not shown) for controlling the release rate of the enhancer from zone 12 to the skin may also optionally be utilized and would be present between the skin 17 and zone 12.

The rate-controlling membrane 13 may be fabricated from permeable, semipermeable or microporous materials which are known in the art to control the rate of agents into and out of delivery devices and having a permeability to the permeation enhancer lower than the matrix material of zone 12. Suitable materials include, but are not limited to, polyethylene, polyvinyl acetate and ethylene vinyl acetate copolymers.

An advantage of the device described in FIG. 2 is that the drug-loaded zone 12 is concentrated at the skin surface rather than throughout the entire mass of a combined drug and enhancer reservoir such as reservoir 2 in FIG. 1. This reduces the amount of drug in the device while maintaining an adequate supply of permeation enhancer.

Superimposed over the drug formulation/enhancer reservoir 11/12 of device 10 is an impermeable backing 15 and an adhesive overlay 16 as described above with respect to FIG. 1. In addition, a strippable liner (not shown) would preferably be provided on the device prior to use as described with respect to FIG. 1 and removed prior to application of the device 10 to the skin 17.

In the embodiments of FIGS. 1 and 2, the carrier or matrix material has sufficient viscosity to maintain its shape without oozing or flowing. If, however, the matrix or carrier is a low viscosity flowable material, the composition can be fully enclosed in a permeable or microporous skin-contacting membrane, as known to the art from U.S. Pat. No. 4,379,454 (noted above), for example.

An example of a presently preferred transdermal delivery device 20 is illustrated in FIG. 3. Device 20 comprises a drug reservoir 22 containing both the drug and the GML/lauryl acetate permeation enhancer. Reservoir 22 is preferably in the form of a matrix containing the drug and the enhancer dispersed therein. Reservoir 22 is sandwiched between a backing layer 24, which is preferably impermeable to both the drug and the permeation enhancer mixture, and an in-line contact adhesive layer 28. In FIG. 3, the drug reservoir 22 is formed of a material, such as a rubbery polymer, that is sufficiently viscous to maintain its shape. The device 20 adheres to the surface of the skin 17 by means of the contact adhesive layer 28. The adhesive for layer 28 should be chosen so that it is compatible and does not interact with any of the drug or, in particular, the GML/lauryl acetate permeation enhancer. The adhesive layer 28 may optionally contain enhancer and/or drug. A strippable liner (not shown) is normally provided along the exposed surface of adhesive layer 28 and is removed prior to application of device 20 to the skin 17. In an alternative embodiment, a rate-controlling membrane (not shown) is present and the drug reservoir 22 is sandwiched between backing layer 24 and the rate-controlling membrane, with adhesive layer 28 present on the skin-side of the rate-controlling membrane.

Various materials suited for the fabrication of the various layers of the transdermal devices of FIGS. 1, 2 or 3 are known in the art or are disclosed in the aforementioned transdermal device patents previously incorporated herein by reference.

The matrix making up the drug/ permeation enhancer reservoir can be a gel or a polymer. Suitable materials are compatible with the drug, GML or other monoglyceride, lauryl acetate, and any other components in the system. Suitable matrix materials include, without limitation, natural and synthetic rubbers or other polymeric material, thickened mineral oil, or petroleum jelly, for example. The matrix is preferably polymeric and is more preferably an anhydrous polymer. A preferred embodiment according to this invention is fabricated from an ethylene vinyl acetate (EVA) copolymer, of the type described in U.S. Pat. No. 4,144,317, and is preferably selected from those EVAs having a vinyl acetate (VA) content in the range of about 9 to 60%, preferably about 28 to 60% VA. Particularly good results may be obtained using EVA of 40% vinyl acetate content.

In addition to a drug and GML/lauryl acetate, which are essential to the invention, the matrix may also contain stabilizers, dyes, pigments, inert fillers, tackifiers, excipients and other conventional components of transdermal delivery devices as are known in the art.

The amounts of the drug that are present in the therapeutic device, and that are required to achieve a therapeutic effect, depend on many factors, such as the minimum necessary dosage of the particular drug; the permeability of the matrix, of the adhesive layer and of the rate-controlling membrane, if present; and the period of time for which the device will be fixed to the skin. There is, in fact, no upper limit to the maximum amounts of drug present in the device. The minimum amount of each drug is determined by the requirement that sufficient quantities of drug must be present in the device to maintain the desired rate of release over the given period of application.

The drug is generally dispersed through the matrix at a concentration in excess of saturation, i.e. at unit activity. The amount of excess is determined by the intended useful life of the system. However, the drug may be present at initial levels below saturation without departing from this invention. Generally, the drug may be present at initially subsaturated levels when: 1) the skin flux of the drug is sufficiently low such that the reservoir drug depletion is slow and small; 2) non-constant delivery of the drug is desired or acceptable; and/or 3) saturation of the reservoir is achieved in use due to migration of water into the reservoir from the skin, where water is abundantly available.

The GML and lauryl acetate mixture is dispersed throughout the matrix, preferably at a concentration sufficient to provide permeation-enhancing concentrations of enhancer in the reservoir throughout the anticipated administration period.

In the present invention, the drug is delivered through the skin or other body surface at a therapeutically effective rate (that is, a rate that provides an effective therapeutic result) and the GML/lauryl acetate dual permeation enhancer is delivered at a permeation-enhancing rate (that is, a rate that provides increased permeability of the application site to the drug) for a predetermined time period.

A preferred embodiment of the present invention is a multilaminate, such as that illustrated in FIG. 3 (either with or without a rate-controlling membrane) wherein reservoir 22 comprises, by weight, 30–90% polymer (preferably EVA having a vinyl acetate content of 40%), 0.01–40% drug, 1–50% GML, and 1–50% lauryl acetate. The in-line adhesive layer 28 comprises an adhesive which is compatible with the permeation enhancer.

A more preferred embodiment of the present invention is a multilaminate, such as that illustrated in FIG. 3 (either with or without a rate-controlling membrane) wherein reservoir 22 comprises, by weight, 30–60% polymer (preferably EVA having a vinyl acetate content of 40%), 0.01–30% drug, 5–40% GML, and 5–40% lauryl acetate.

The devices of this invention can be designed to effectively deliver a drug for an extended time period of up to 7 days or longer. Seven days is generally the maximum time limit for application of a single device because the skin site is adversely affected by a period of occlusion greater than 7 days. Where it is desired to have drug delivery for greater than 7 days (such as, for example, when a hormone is being applied for a contraceptive effect), when one device has been in place on the skin for its effective time period, it is replaced with a fresh device, preferably on a different skin site.

The transdermal therapeutic devices of the present invention are prepared in a manner known in the art, such as by those procedures, for example, described in the transdermal device patents listed previously herein. The following examples are offered to illustrate the practice of the present invention and are not intended to limit the invention in any manner.

EXAMPLE 1

The effect of various permeation enhancer mixtures on the transdermal flux of alprazolam was studied. The drug/permeation enhancer reservoirs were prepared by mixing ethylene vinyl acetate having a vinyl acetate content of 40 percent ("EVA 40", USI Chemicals, Illinois) in an internal mixer (Brabender type) until the EVA 40 pellets fused. Alprazolam, GML, glycerol monooleate (GMO), lauryl acetate (Penta International Corp., Livingston, N.J.), lauryl lactate, and myristyl lactate were then added as shown in Table 1. The mixture was blended, cooled, and calendered to a 5 mil thick film.

The film was then laminated to a Medpar® (3M, St. Paul, Minn.) backing on one side and an acrylate contact adhesive (3M Acrylic MSP 041991P) on the opposite side. The laminate was then cut into 2.54 cm$^2$ circles using a steel punch.

TABLE 1

| Drug/Permeation Enhancer Reservoir Composition (weight percent) | |
|---|---|
| FORMULATION | WEIGHT PERCENT |
| Alprazolam/GML/lauryl acetate/EVA 40 | 15/20/12/53 |
| Alprazolam/GML/lauryl lactate/EVA 40 | 15/20/12/53 |
| Alprazolam/GML/lauryl lactate/EVA 40 | 15/13/27/45 |
| Alprazolam/GMO/EVA 40 | 15/30/55 |
| Alprazolam/GMO/lauryl lactate/EVA 40 | 15/20/12/53 |
| Alprazolam/GMO/myristyl lactate/EVA 40 | 15/20/12/53 |

Circular pieces of human epidermis were mounted on the receptor compartment of horizontal permeation cells with the stratum corneum facing the donor compartment of the cell. The release liner of the laminate was removed and the systems were centered over the stratum corneum side of the epidermis. The donor compartment was then clamped with the receptor compartment. A known volume of receptor solution (20 ml, 0.01M potassium phopsphate pH 6+2% isopropyl alcohol) was equilibrated at 35° C. and placed in the receptor compartment. Air bubbles were removed from the receptor compartment, the cell was capped and placed in a water bath shaker at 35° C.

Figure 4:
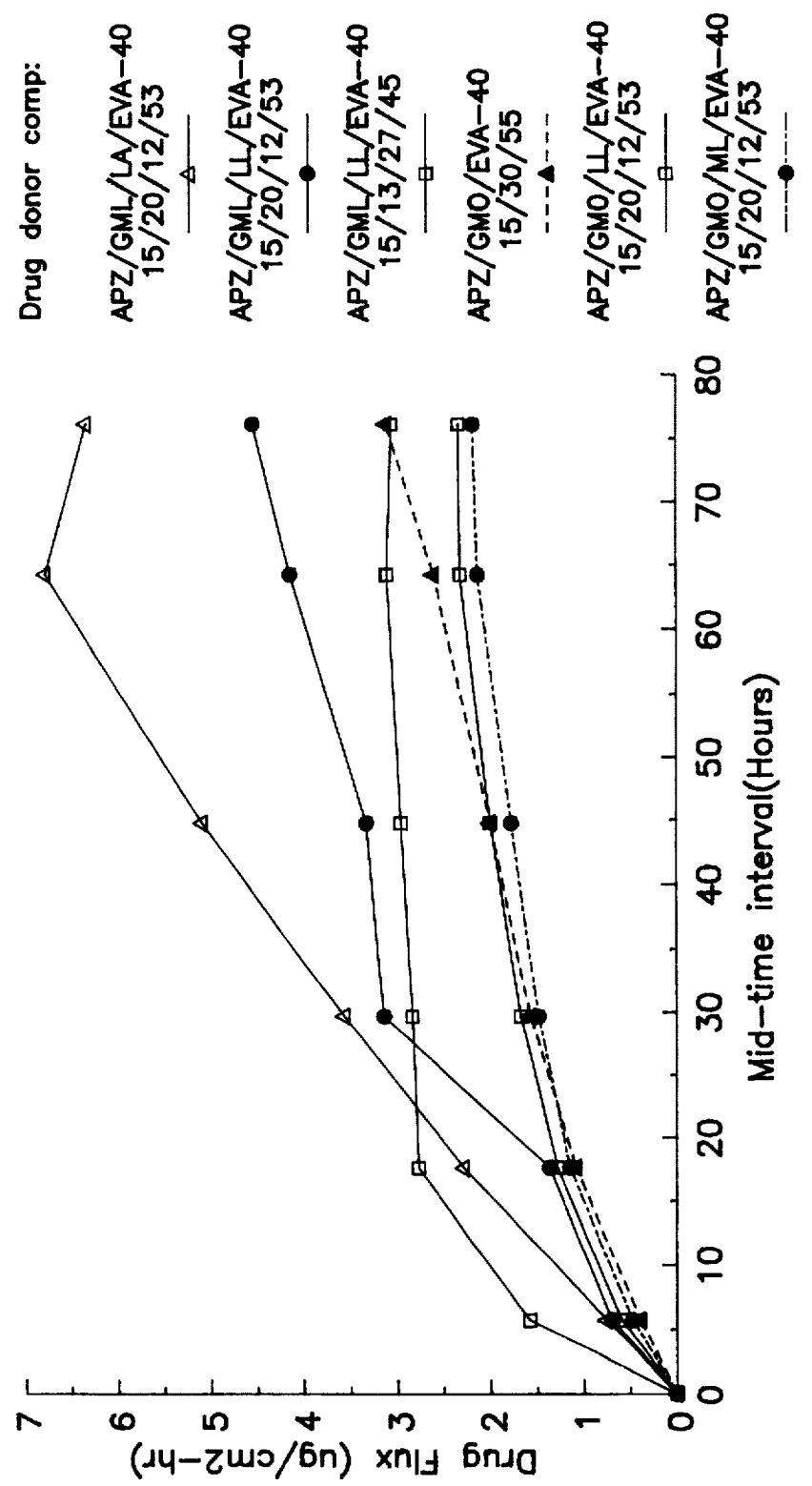
FIG. 4 is a graph of the flux of alprazolam through human epidermis at 35° C. from systems using various enhancers.

At given time intervals, the entire receptor solution was removed from the cells and replaced with an equal volume of fresh receptor solutions previously equilibrated at 35° C. The receptor solutions are stored in capped vials at 4° C. until assayed for alprazolam content by high performance liquid chromatography (HPLC). From the drug concentration and the volume of the receptor solutions, the area of permeation and the time interval, the flux of the drug through the epidermis was calculated as follows: (drug concentration×volume of receptor)/(area×time)=flux (μg/cm$^2$·hr). The transdermal fluxes of the various systems is shown in FIG. 4. As demonstrated in FIG. 4, the system comprising the GML/lauryl acetate permeation enhancer mixture achieved the greatest flux of alprazolam through skin.

EXAMPLE 2

The effect of GML and various cosolvents on the transdermal flux of oxybutynin was determined. The drug/permeation enhancer reservoirs, having the compositions shown in Table 2, were prepared by the procedure described in Example 1.

TABLE 2

Drug/Permeation Enhancer Reservoir Composition (weight percent)

| DRUG RESERVOIR | WEIGHT PERCENT |
|---|---|
| oxybutynin base/GML/EVA | 25/20/55 |
| oxybutynin base/GML/ceraphyl 31/EVA | 25/20/12/43 |
| oxybutynin base/GML/lauryl lactate/EVA | 25/20/12/43 |
| oxybutynin base/GML/methyl laurate/EVA | 25/20/12/43 |
| oxybutynin base/GML/lauryl acetate/EVA | 25/20/12/43 |

The drug reservoirs were then laminated to a water vapor permeable Sontara® spun laced polyester backing (code 80632B, DuPont, Wilmington Del.) on one side and a 1 mil thick Celgard® (Hoecsht Celanese, Charlotte, N.C.) film tie layer (microporous polypropylene) on the other. The laminate was then cut into 1.98 cm² circles using a steel punch. The punched systems were then weighed and placed in a 35° C. oven to equilibrate.

The in vitro transdermal oxybutynin permeation rates through human epidermis from the systems described above were determined. The systems tested were masked so that none of the device, except for the skin contacting surface, would be exposed to the receptor solution. For each system tested, the release liner was removed and the oxybutynin-releasing surface was centered and placed against the stratum corneum side of a disc of human epidermis which had been blotted dry just prior to use. The excess epidermis was wrapped around the device.

The assembly was then attached to the flat side of a Teflon® holder of a release rate rod using wire and nylon mesh. The rod with the system attached was placed into a 50 cc test tube filled with a known volume of receptor solution (0.05M phosphate solution, pH 6.0). Constant vertical stirring was accomplished by attaching the rod to a crossrod connected to an agitator that reciprocates the rod and system vertically in the test tube. The receptor solution was maintained at 35° C.

At given time intervals, the entire receptor solution was removed from the test tube and replaced with an equal volume of fresh receptor solution previously equilibrated at 35° C. The receptor solutions were stored in capped vials and refrigerated until assayed for oxybutynin content by HPLC.

Figure 5:
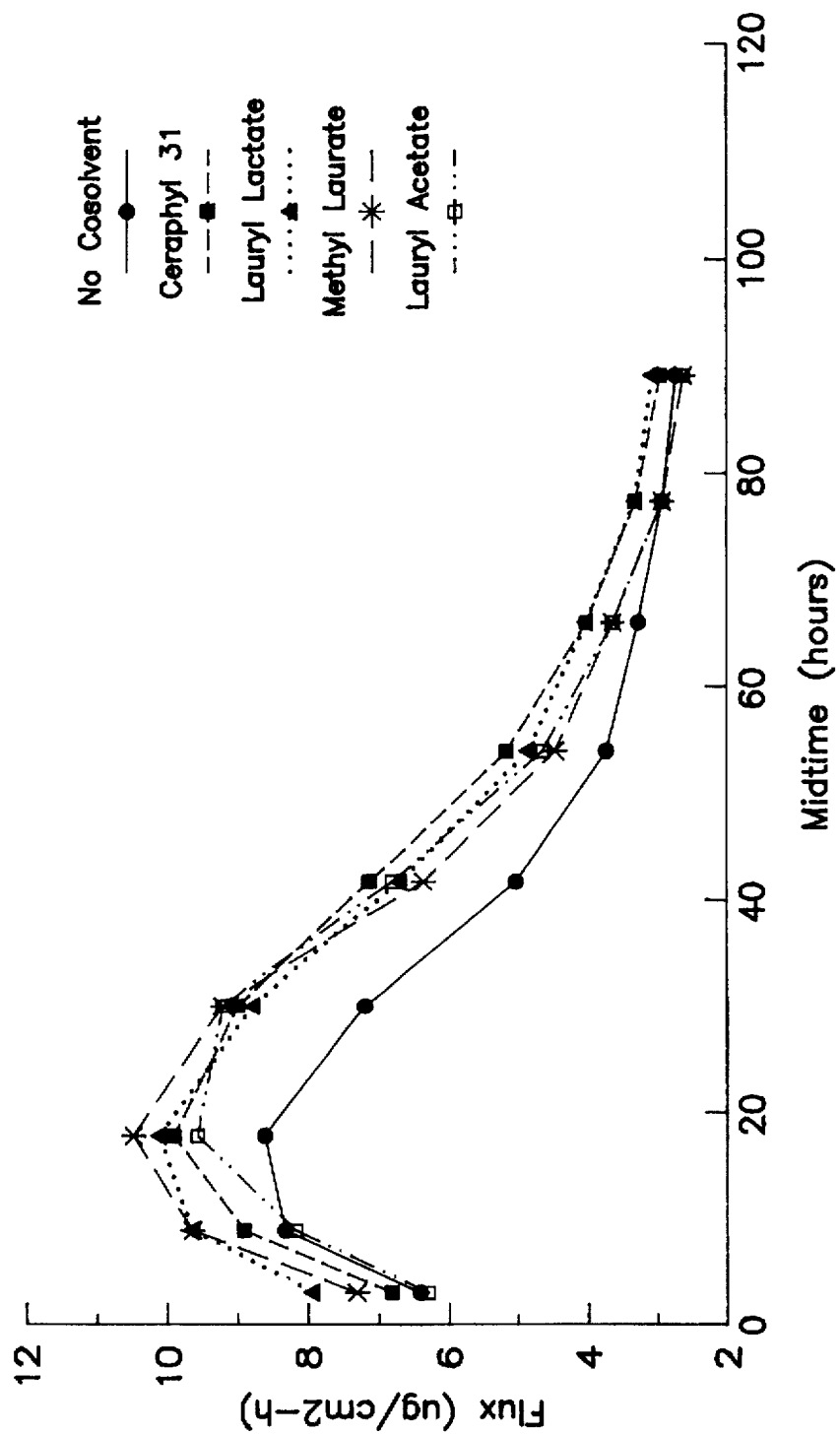
FIG. 5 is a graph of the flux of oxybutynin through human epidermis using various cosolvents for GML.

The transdermal flux of oxybutynin through human epidermis from these systems is shown in FIG. 5. As demonstrated in FIG. 5, the resultant skin flux of the GML/lauryl acetate formulation was greater than that of GML alone.

EXAMPLE 3

Systems comprising permeation enhancer mixtures of GML/lauryl acetate were compared to systems comprising mixtures of GML/lauryl lactate to observe the effect on the transdermal flux of alprazolam. Drug/permeation enhancer reservoirs, having the compositions shown in Table 3, were prepared by the procedures described in Example 1.

TABLE 3

Drug/Permeation Enhancer Reservoir Composition (weight percent)

| FORMULATION | WEIGHT PERCENT |
|---|---|
| Alprazolam/GML/lauryl acetate/EVA 40 | 15/20/12/53 |
| Alprazolam/GML/lauryl acetate/EVA 40 | 15/13/27/45 |
| Alprazolam/GML/lauryl acetate/EVA 40 | 15/15/25/45 |
| Alprazolam/GML/lauryl lactate/EVA 40 | 15/20/12/53 |
| Alprazolam/GML/lauryl lactate/EVA 40 | 15/13/27/45 |
| Alprazolam/GML/lauryl lactate/EVA 40 | 15/15/25/45 |
| Alprazolam/EVA 40 | 15/85 |

Figure 6:
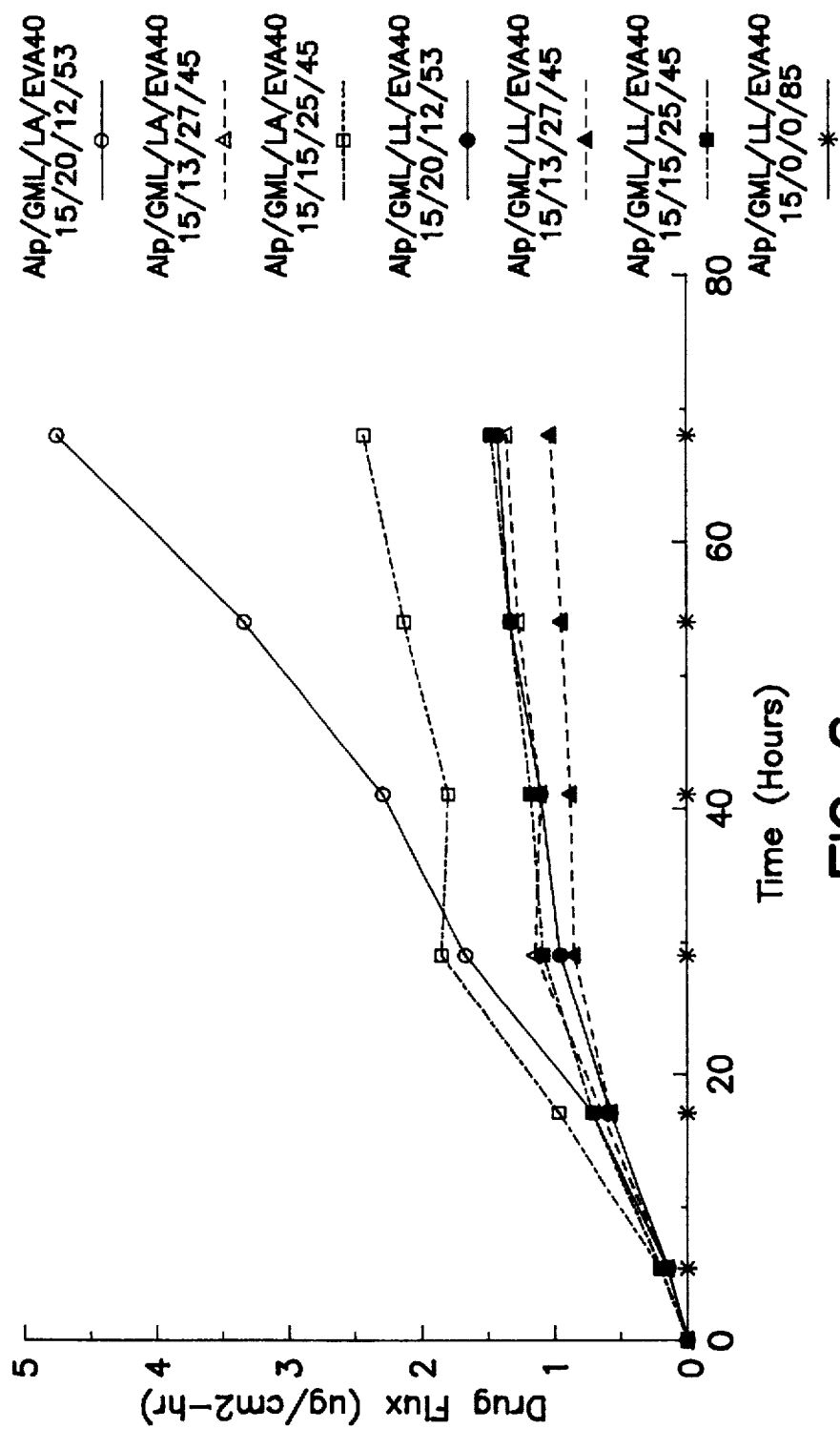
FIG. 6 is a graph of the flux of alprazolam through human epidermis at 35° C. from systems using various concentrations of FML with lauryl acetate or lauryl lactate.

These reservoir formulations were then used in transdermal flux studies using the same apparatus and procedures described in Example 1. The effect of the concentration of GML, lauryl acetate, and lauryl lactate on the flux of alprazolam through human epidermis from EVA 40 monoliths at 35° C. is shown in FIG. 6. As demonstrated in FIG. 6, the GML/lauryl acetate mixture provided a superior flux of alprazolam through skin of up to three times that of a GML/lauryl lactate mixture. The 15/25 mixture of GML/lauryl acetate reached steady state flux the quickest.

EXAMPLE 4

Drug/permeation enhancer reservoirs were prepared using the procedure of Example 3, substituting testosterone for alprazolam. The composition of the drug reservoirs is shown in Table 4.

TABLE 4

Drug/Permeation Enhancer Reservoir Composition (weight percent)

| FORMULATION | WEIGHT PERCENT |
|---|---|
| Testosterone/GML/lauryl acetate/EVA 40 | 15/20/12/53 |
| Testosterone/GML/lauryl acetate/EVA 40 | 15/13/27/45 |
| Testosterone/GML/lauryl acetate/EVA 40 | 15/15/25/45 |
| Testosterone/GML/lauryl lactate/EVA 40 | 15/20/12/53 |
| Testosterone/GML/lauryl lactate/EVA 40 | 15/13/27/45 |
| Testosterone/GML/lauryl lactate/EVA 40 | 15/15/25/45 |
| Testosterone/EVA 40 | 15/85 |

Figure 7:
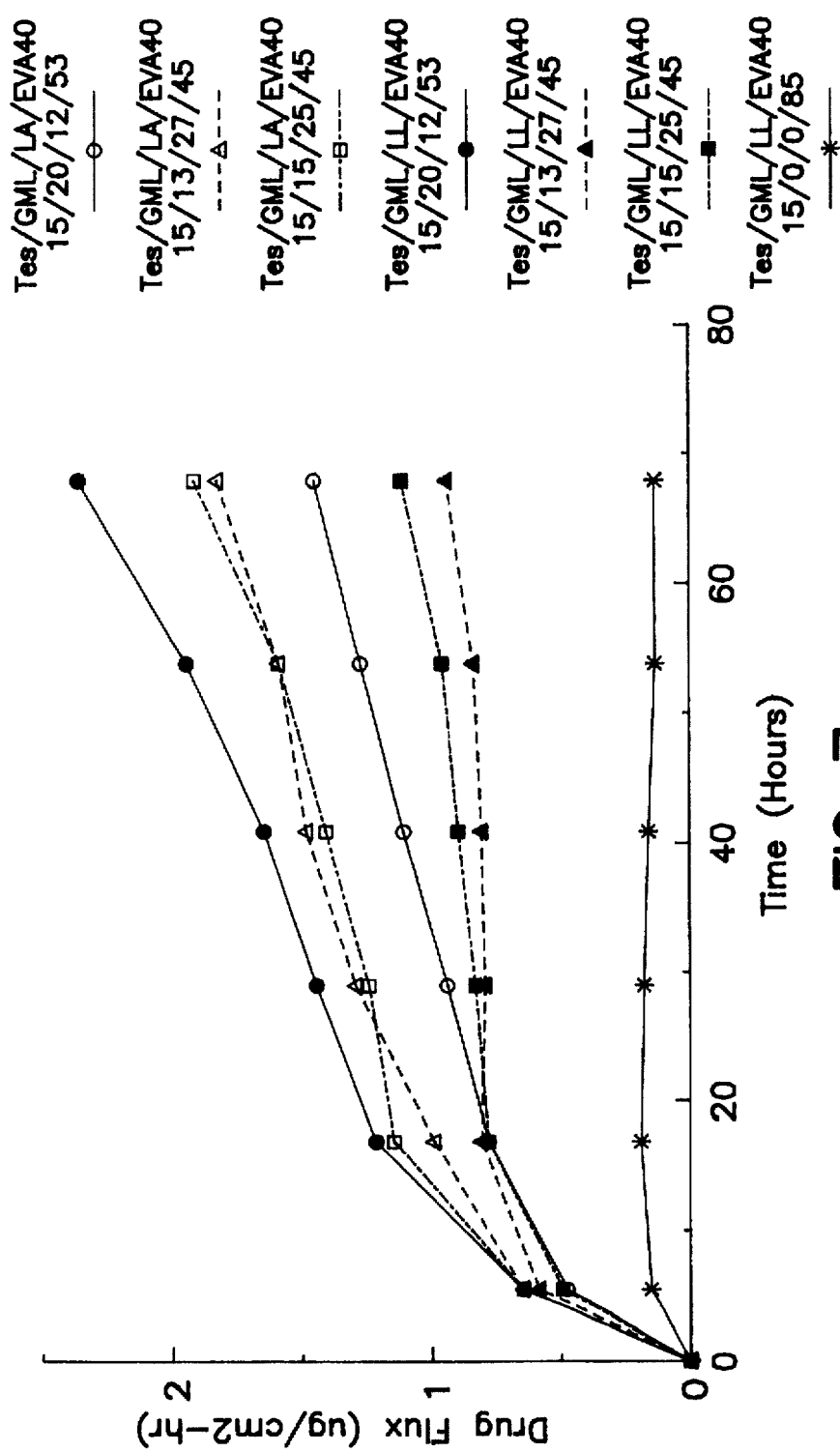
FIG. 7 is a graph of the flux of testosterone through human epidermis at 35° C. from systems using various concentrations of GML with lauryl acetate or lauryl lactate.

The skin flux experiment described in Example 1 was repeated for these systems, substituting 0.1% phenol as the receptor solution. The effect of the concentration of GML, lauryl acetate, and lauryl lactate on the flux of testosterone through human epidermis from EVA 40 monoliths at 35° C. is shown in FIG. 7.

The invention has been described in detail with particular reference to certain preferred embodiments thereof, but it will be understood that variations and modifications can be affected within the scope and spirit of the invention.

What is claimed is:

1. A composition of matter for transdermally delivering at least one drug at a therapeutically effective rate by permeation through a body surface or membrane comprising, in combination:

(a) at least one drug; and (b) a permeation enhancer comprising 1-50 wt % lauryl acetate and 1-50 wt % of a monoglyceride, wherein the agent and permeation enhancer are dispersed within a carrier.

2. A composition according to claim 1 wherein the monoglyceride is glycerol monolaurate.

3. A composition according to claim 1 wherein the drug is present in an amount in excess of its saturation in the carrier.

4. A device for the transdermal administration of at least one drug at a therapeutically effective rate by permeation through a body surface or membrane, comprising:
   a) drug reservoir comprising at least one drug and a permeation enhancer mixture comprising 1–50 wt % lauryl acetate and 1–50 wt % of a monoglyceride;
   b) a backing on or adjacent the skin distal surface of the drug reservoir;
   c) means for maintaining the reservoir in drug- and permeation enhancer-transmitting relation with the body surface or membrane.

5. A device according to claim 4 wherein the monoglyceride is glycerol monolaurate.

6. A device according to claim 4 wherein the drug is selected from the group consisting of alprazolam, testosterone, oxybutynin, and nandrolone.

7. A device according to claim 4 wherein the means for maintaining the reservoir in drug- and permeation enhancer-transmitting relation with the body surface or membrane is a contact adhesive.

8. A device according to claim 4 wherein the drug reservoir comprises:
   i) 0.01–30% by weight of a drug,
   ii) 5–40% by weight lauryl acetate,
   iii) 5–40% by weight glycerol monolaurate, and
   iv) 30–60% by weight ethylene vinyl acetate copolymer.

9. A device for the transdermal administration of at least one drug at a therapeutically effective rate by permeation through a body surface or membrane, comprising:
   a) a first reservoir comprising at least one drug and a permeation enhancer mixture comprising 1–50 wt % lauryl acetate and 1–50 wt % of a monoglyceride;
   b) a second reservoir comprising an additional amount of the permeation enhancer mixture;
   c) a rate controlling membrane between the first and second reservoirs;
   d) a backing on or adjacent the skin distal surface of the first reservoir; and
   e) means for maintaining the reservoir in drug- and permeation enhancer-transmitting relation with the body surface or membrane.

10. A device according to claim 9 wherein the monoglyceride is glycerol monolaurate.

11. A device according to claim 9 wherein the drug is selected from the group consisting of alprazolam, testosterone, oxybutynin, and nandrolone.

12. A method for the transdermal administration of at least one drug at a therapeutically effective rate comprising simultaneously coadministering to a body surface or membrane a drug and a permeation enhancer mixture comprising 1–50 wt % lauryl acetate and 1–50 wt % of a monoglyceride.

13. A method according to claim 12 further comprising maintaining said coadministration of drug and permeation enhancing mixture for a period of time sufficient to produce a beneficial effect.

14. A method according to claim 12 wherein the monoglyceride is glycerol monolaurate.

15. A method according to claim 12 wherein the drug is selected from the group consisting of alprazolam, testosterone, oxybutynin, and nandrolone.

16. A composition according to claim 1 wherein the drug is selected from the group consisting of alprazolam, testosterone, oxybutynin, and nandrolone.

17. A composition according to claim 1 wherein the lauryl acetate is at least about 97% pure.

18. A device according to claim 4 wherein the lauryl acetate is at least about 97% pure.

19. A device according to claim 8 wherein the drug reservoir comprises 20% by weight glycerol monolaurate and 12% by weight lauryl acetate.

20. A device according to claim 9 wherein the lauryl acetate is at least about 97% pure.

21. A device according to claim 9 wherein the first reservoir comprises 20% by weight glycerol monolaurate and 12% by weight lauryl acetate.

22. A method according to claim 12 wherein the lauryl acetate is at least about 97% pure.

23. A composition of matter for transdermally administering at least one drug at a therapeutically effective rate by permeation through a body surface or membrane comprising, in combination:
   (a) 0.01–30 wt % of at least one drug; and
   (b) a permeation enhancer comprising 5–40 wt % lauryl acetate and 5–40 wt % glycerol monolaurate wherein the agent and permeation enhancer are dispersed within a carrier.

24. A device for the transdermal administration of at least one drug at a therapeutically effective rate by permeation through a body surface or membrane, comprising:
   a) a drug reservoir comprising:
      i) 0.01–30 wt % of at least one drug;
      ii) 5–40 wt % lauryl acetate;
      iii) 5–40 wt % glycerol monolaurate; and
      iv) 30–90 wt % of a polymeric carrier;
   b) a backing on or adjacent the skin distal surface of the drug reservoir;
   c) means for maintaining the reservoir in drug- and permeation enhancer-transmitting relation with the body surface or membrane.

25. A device according to claim 24 wherein the drug reservoir comprises 30–60% by weight of a polymeric carrier comprising ethylene vinyl acetate copolymer having a vinyl acetate content of 9–60%.

26. A device for the transdermal administration of at least one drug at a therapeutically effective rate by permeation through a body surface or membrane, comprising:
   a) a first reservoir comprising:
      i) 0.01–30 wt % of at least one drug;
      ii) 5–40 wt % lauryl acetate;
      iii) 5–40 wt % glycerol monolaurate; and
      iv) 30–90 wt % of a polymeric carrier;
   b) a second reservoir comprising an additional amount of glycerol monolaurate and lauryl acetate;
   c) a rate controlling membrane between the first and second reservoirs;
   d) a backing on or adjacent the skin distal surface of the first reservoir; and
   e) means for maintaining the reservoir in drug- and permeation enhancer-transmitting relation with the body surface or membrane.

27. A device according to claim 24 wherein the first reservoir comprises 30–60% by weight of a polymeric carrier comprising ethylene vinyl acetate copolymer having a vinyl acetate content of 9–60%.

28. A device according to claim 24 wherein the drug is selected from the group consisting of alprazolam, testosterone, oxybutynin, and nandrolone.

29. A device according to claim 24 wherein the lauryl acetate is at least about 97% pure.

30. A device according to claim 26 wherein the drug is selected from the group consisting of alprazolam, testosterone, oxybutynin, and nandrolone.

31. A device according to claim 26 wherein the lauryl acetate is at least about 97% pure.

32. A method for the transdermal administration of at least one drug at a therapeutically effective rate comprising simultaneously coadministering to a body surface or membrane at least one drug and a permeation enhancer mixture comprising 1–50 wt % lauryl acetate and 1–50 wt % glycerol monolaurate.

33. A method according to claim 32 wherein the drug is selected from the group consisting of alprazolam, testosterone, oxybutynin, and nandrolone.

34. A method according to claim 32 wherein the lauryl acetate is at least about 97% pure.

* * * * *